US011642524B2

(12) United States Patent
Djalilian et al.

(10) Patent No.: US 11,642,524 B2
(45) Date of Patent: May 9, 2023

(54) METHODS AND SYSTEMS FOR TREATING TINNITUS WITH TRANSTYMPANIC ELECTRICAL STIMULATION

(71) Applicant: THE REGENTS OF THE UNIVERSITY OF CALIFORNIA, Oakland, CA (US)

(72) Inventors: Hamid R. Djalilian, Orange, CA (US); Fan-Gang Zeng, Irvine, CA (US); Harrison Lin, Orange, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 180 days.

(21) Appl. No.: 16/859,802

(22) Filed: Apr. 27, 2020

(65) Prior Publication Data
US 2020/0338349 A1 Oct. 29, 2020

Related U.S. Application Data (60) Provisional application No. 62/838,686, filed on Apr. 25, 2019.

(51) Int. Cl.
*A61N 1/36* (2006.01)
(52) U.S. Cl.
CPC .............................. *A61N 1/36038* (2017.08)
(58) Field of Classification Search
CPC ................................................... A61N 1/36038
See application file for complete search history.

(56) References Cited

U.S. PATENT DOCUMENTS

| 2002/0029070 | A1* | 3/2002 | Leysieffer | .......... A61N 1/36036 607/57 |
| 2010/0305677 | A1* | 12/2010 | Schmidt | ............... A61N 1/0541 607/137 |
| 2021/0339022 | A1* | 11/2021 | Zilbershlag | ........ A61N 1/36038 |

OTHER PUBLICATIONS

Zeng, F. et al., Tinnitus Treatment Using Noninvasive and Minimally Invasive Electric Stimulation: Experimental Design and Feasibility, Trends in Hearing, pp. 1-12, vol. 23, Dec. 5, 2018, Irvine, California U.S.A.
Zheng, F. et al. Tinnitus treatment with precise and optimal electric stimulation: opportunities and challenges. Current Opinon. Oct. 2015, 382-387, vol. 23, No. 5, Wolters Kluwer Health, Inc., Irvine, U.S.A.
Perez, R. et al. Multiple Electrostimulation Treatments to the Promontory for Tinnitus, Otology & Neurotology, 2015, 366-372, vol. 36, No. 2, Otology & Neurotology, Inc., Michigan, U.S.A.
Wenzel, G. et al. Non-penetrating round window electrode stimulation for tinnitus therapy followed by cochlear implantation, Eur Arch Otorhinolaryngol, Dec. 6, 2014, Springer-Verlag Berlin Heidelberg, Luneburg, Germany.

* cited by examiner

*Primary Examiner* — Joseph M Dietrich
(74) *Attorney, Agent, or Firm* — Nguyen Tarbet LLC (57) ABSTRACT

An electrical stimulation system that provides for transtympanic stimulation of the inner ear that can be used for safely and effectively treating tinnitus. The electrical stimulation system of the present invention may be fully implantable or partially implantable. The system features an electrode placed on the round window membrane. An external portion provides the power to the electrode, which can stimulate the inner ear via the round window as needed by the patient. The present invention also features methods of treating tinnitus using the electrical stimulation system described herein.

19 Claims, 5 Drawing Sheets

A. ANATOMICAL ARRANGEMENT

FIG. 7

METHODS AND SYSTEMS FOR TREATING TINNITUS WITH TRANSTYMPANIC ELECTRICAL STIMULATION

CROSS-REFERENCES TO RELATED APPLICATIONS

This application is a non-provisional and claims benefit of U.S. Provisional Application No. 62/838,686 filed Apr. 25, 2019, the specification of which is incorporated herein in its entirety by reference.

STATEMENT REGARDING FEDERALLY SPONSORED RESEARCH OR DEVELOPMENT

This invention was made with government support under Grant No. NIH 5R01 DC015587 awarded by National Institute on Deafness and Other Communication Disorders. The government has certain rights in the invention.

BACKGROUND OF THE INVENTION

Field of the Invention

The invention relates to tinnitus, more particularly to methods and systems that use electrical stimulation to stimulate the inner ear or auditory nerve for treating tinnitus.

Background Art

Tinnitus is the perception of sound in the absence of sound. There are currently between 30-50 million in the US who have tinnitus and 2-3 million are disabled by the tinnitus. Currently, the only solution for treating tinnitus is using sound therapy. However, sound therapy is only partially effective in tinnitus treatment because acoustic stimulation cannot activate the deafferented auditory nerve fibers that may be the root cause of tinnitus generation. For patients who have lost hearing, a cochlear implant can be placed into the inner ear to restore hearing. A cochlear implant, which delivers electrical current to the hearing nerve cells, can suppress tinnitus for a majority of patients with severe hearing loss and tinnitus. However, most patients with tinnitus are not candidates for cochlear implantation.

Non-invasive transcranial or minimally-invasive transtympanic electric stimulation may be considered as a treatment option because it can activate the detached nerve while posing minimal risk of damaging hearing. However, no protocols or devices have been widely accepted by the scientific community or clinically approved by the United States Food and Drug Administration at present. Certain factors have significantly contributed to the lack of progress in translating electric stimulation for tinnitus treatment. First, there is no clear and unified scientific rationale to guide technological development. For example, some groups have sought to decrease spontaneous activity in the auditory nerve, while other groups have sought to increase spontaneous activity in the auditory nerve. Second, safety is an important concern in electric stimulation for tinnitus. Third, the optimal parameters of electric stimulation have not been universally accepted. Finally, practicality is a significant limiting factor. There is not a single electric stimulator that is specifically designed and commercially available to meet the need for tinnitus treatment. Previous studies used stimulators for pain management. In addition, stable electrode contact is difficult with either tympanic or transtympanic stimulation.

Inventors have surprisingly designed an electrical stimulation system that provides for transtympanic (through the ear drum) stimulation of the inner ear, which can be used for safely and effectively treating tinnitus. The electrical stimulation system of the present invention may result in complete suppression of tinnitus in some patients. The present invention also features methods of treating tinnitus using the electrical stimulation system described herein.

BRIEF SUMMARY OF THE INVENTION

The present invention features methods and electrical stimulation systems for treating tinnitus with transtympanic electrical stimulation. The electrical stimulation system of the present invention may be semi-implantable or fully implantable and delivers electrical stimulation to the inner ear to suppress tinnitus.

For example, the present invention features an electrical stimulation system comprising an electrode for directly contacting a round window membrane of an ear; and a microprocessor disposed in a housing portion to create a receiver, wherein the microprocessor is operatively connected to the electrode. The microprocessor sends a signal to the electrode to cause the electrode to deliver electrical stimulation to the round window membrane. The system further comprises a power source operatively connected to the microprocessor and the electrode. The electrical stimulation delivered by the electrode helps reduce or eliminate tinnitus.

In some embodiments, the system is semi-implantable. In some embodiments, the system is fully implantable. In some embodiments, a user can turn the electrode on or off as needed. In some embodiments, a control device is wirelessly operatively connected to the microprocessor, the control device functions to turn on and off the electrode.

The present invention also features a method of treating tinnitus in patient in need thereof. The method may comprise implanting the electrical stimulation system of the present invention such that the electrode is in direct contact with the round window without completely obstructing the round window and immobilizing the receiver in the ear of the patient such that the electrode does not move around. The user can turn electrical stimulation on and off as needed to help reduce or eliminate tinnitus.

One of the unique and inventive technical features of the present invention is the position of the receiver adjacent or near-adjacent to the electrode. Without wishing to limit the invention to any theory or mechanism, it is believed that the technical feature of the present invention advantageously provides for time-efficient and less invasive implantation of the tinnitus treatment device of the present invention. None of the presently known prior references or work has the unique inventive technical feature of the present invention. Furthermore, the feature of the present invention is counterintuitive. The reason that it is counterintuitive is because the prior references teach away from the present invention. For example, prior systems teach the implantation of a receiver under the scalp near the ear and connecting said receiver to the electrode in the middle ear. The present invention utilizes a relatively small receiver immobilized in the middle ear to allow for implantation through only one incision. Therefore, the present invention is counterintuitive. Furthermore, the inventive technical features of the present invention contributed to a surprising result. For example, one skilled in the art would expect a tinnitus treatment device utilizing the relatively small receiver to not be able to provide enough power to stimulate an inner ear of a patient and provide tinnitus relief. Surprisingly, despite the relatively small receiver, the tinnitus treatment device of the present invention is able to power the electrode enough to stimulate the inner ear of the patient and provide tinnitus relief. Therefore, the present invention is counterintuitive.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

DETAILED DESCRIPTION OF THE INVENTION

Following is a list of elements corresponding to a particular element referred to herein:
100 electrical stimulation system
110 electrode
120 receiver
125 anchors
130 transmitter
210 round window
220 middle ear
230 ear canal The present invention features methods and electrical stimulation systems for treating tinnitus with transtympanic electrical stimulation. The electrical stimulation system of the present invention may be semi-implantable or fully implantable and delivers electrical stimulation to the inner ear to suppress tinnitus.

Figure 5:
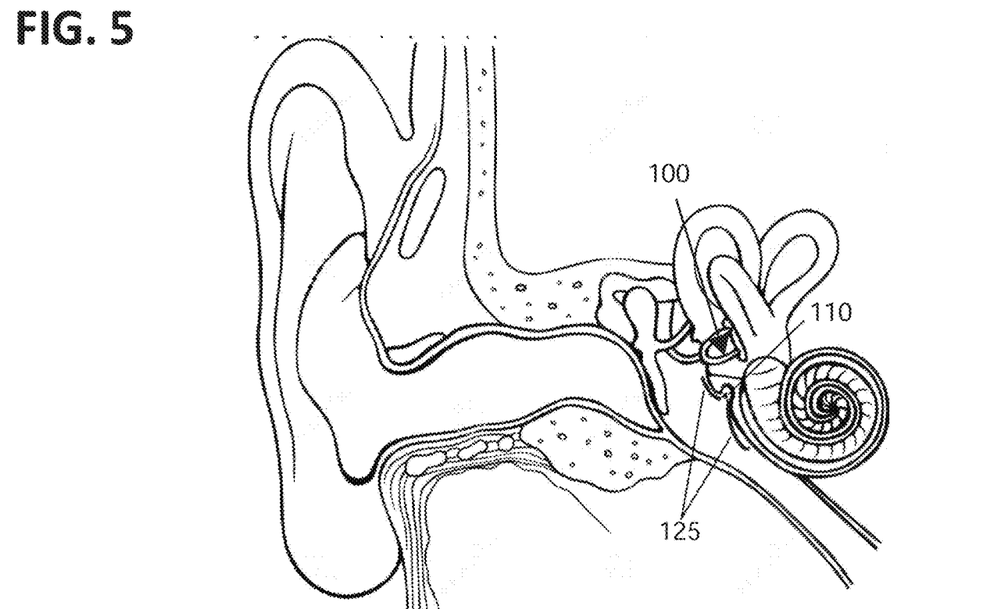
FIG. 5 shows a schematic view of the ear. The electrode is shown, as well as the anchors that hold the electrode in place.
Figure 6:
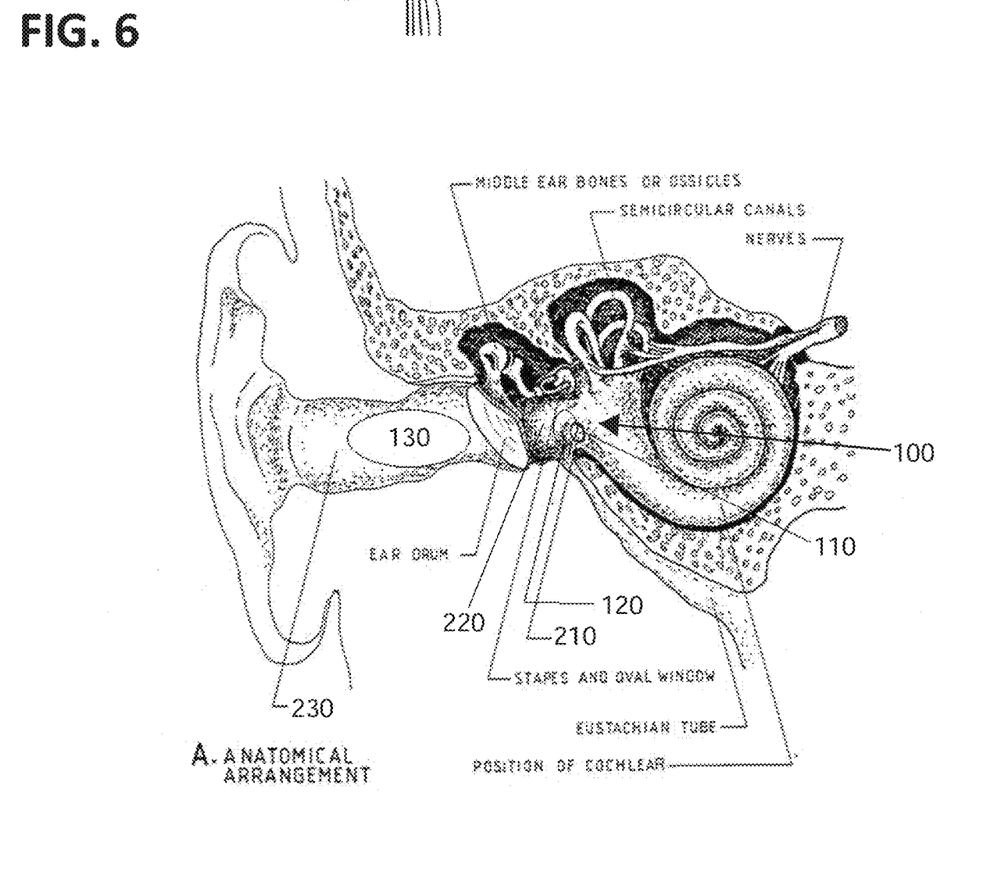
FIG. 6 shows a schematic view of the ear. The electrode and a receiver are shown, as well as a stimulator in the ear canal.

The electrical stimulation system may comprise an electrode that may be placed in contact with a round window membrane (see FIG. 5, FIG. 6) without fully covering the round window. In some embodiments, the electrode may be placed on a surface of an outer wall of a cochlea. In other embodiments, the electrode may be placed in contact with a middle ear. The electrode may be 10 mm or less in diameter. The system also comprises a microprocessor disposed in a receiver operatively connected to the electrode. The receiver may be 10 mm or less in diameter. The receiver may be disposed adjacent or near-adjacent to the electrode. The receiver may be 0.1 to 100 mm away from the electrode. The microprocessor can control the electrode as necessary, wherein the electrode stimulates the inner ear via the round window, the middle ear, and/or an inner ear, to effectively help suppress or eliminate tinnitus. The signal to the electrode may be transmitted optically. The electrical stimulation system may further comprise a transmitter comprising a power source operatively connected to the receiver. The transmitter may be disposed in an ear canal of the patient. In some embodiments, the patient can control the electrode via a wireless transmission system operatively connected to the microprocessor. For example, the patient can turn the system on and off as needed. Additionally, the wireless transmission system may be capable of toggling, controlling, or changing frequency, shape, duration, pulse, and/or amplitude of the current delivered by the system. The wireless transmission system may be an external application on a phone or computer.

The system is designed, e.g., with components such as attachment arms that provide tension, so that the electrode maintains contact with the round window membrane without completely obstructing it or moving around. In some embodiments, the system of the present invention may be capable of magnetic stimulation.

Figure 7:
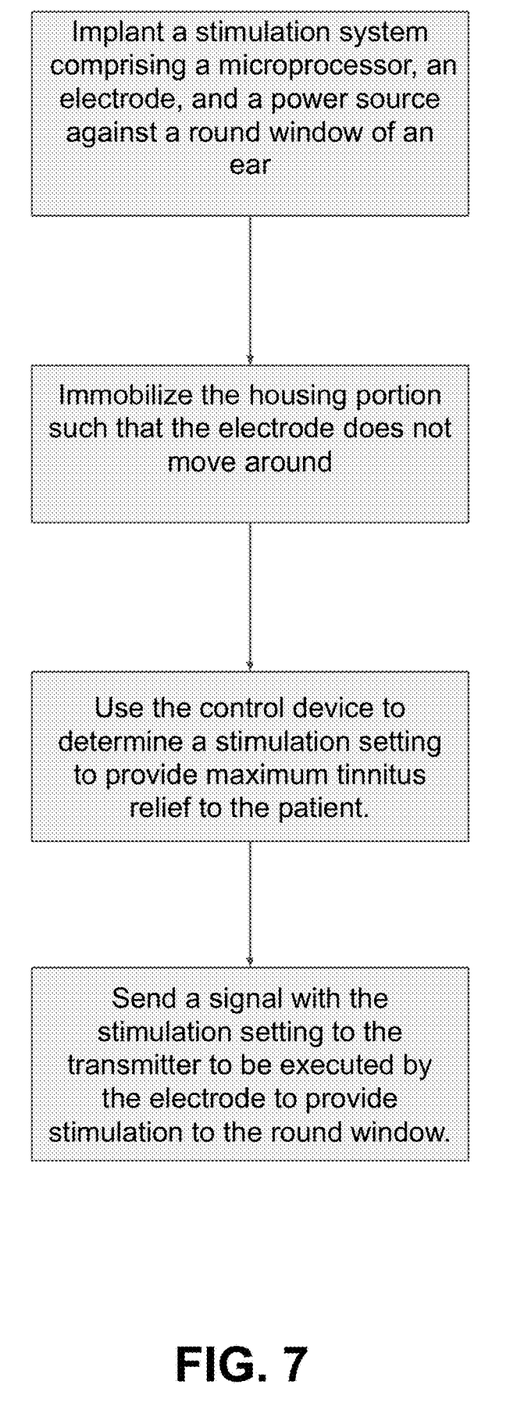
FIG. 7 shows a flow chart of a method of usage of a stimulation system of the present invention.

Referring now to FIG. 7, the present invention features a method of treating tinnitus in a patient in need thereof. The method may comprise implanting a stimulation system. The stimulation system may comprise an electrode or electrodes for directly contacting a middle ear or inner ear, a microprocessor disposed in a receiver operatively connected to the electrode for sending a first signal to the electrode to cause the electrode to deliver stimulation to a portion of an ear, and a transmitter comprising a power source operatively connected to the microprocessor and the electrode. In some embodiments, the electrode is in direct contact with a round window without completely obstructing the round window. The method may further comprise immobilizing the receiver in the ear of the patient such that the electrode does not move around. The method may further comprise using a control device to determine a stimulation setting to provide maximum tinnitus relief to the patient and sending a signal with the stimulation setting to the transmitter to be executed by the electrode to provide stimulation to the round window. In some embodiments, the control device is a wireless transmission system with an control application, such as a phone or computer. The stimulation system may then be deactivated to stop delivering stimulation to the patient's ear. In some embodiments, the stimulation system sends a minimum amount of stimulation to the ear to remedy tinnitus. In some embodiments, the electrode delivers trans-tympanic stimulation.

Without wishing to limit the present invention to any theory or mechanism, it is believed that the system of the present invention is advantageous because it does not require surgery for implantation. For example, in some embodiments, just a small incision in the eardrum is necessary for proper placement of the electrode.

EXAMPLE

The following is a non-limiting example of the present invention. It is to be understood that said example is not intended to limit the present invention in any way. Equivalents or substitutes are within the scope of the present invention.

The present study investigated the short-term effect of a limited set of electric stimulation parameters on tinnitus in 10 adults (T1 through T10) with various types of chronic tinnitus (≥6 months). As will be shown below, five subjects showed nearly 100% tinnitus suppression in response to 2- to 10-minute electric stimulation. The total and prolonged tinnitus suppression in two subjects (T3 and T10) further suggested that round window stimulation be further explored as potentially a long-term solution.

Non-Invasive Electric Stimulation

Figure 1:
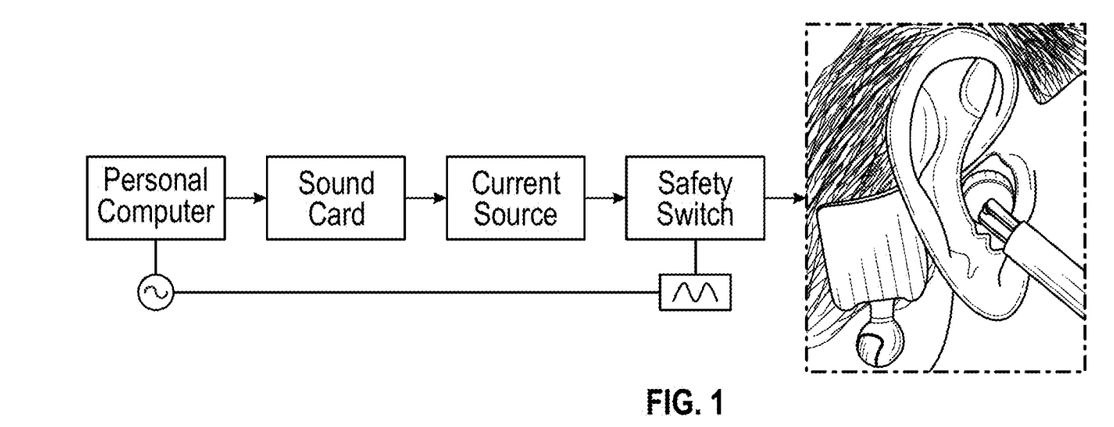
FIG. 1 shows a schematic for electric stimulation. The right panel shows a setup for non-invasive electric stimulation in which a gold-plated tiptrode is inserted in the ear canal and a plate electrode is placed on the mastoid.

FIG. 1 shows a block diagram of a custom-made research interface for electric stimulus generation and control. A personal computer was used to generate digital stimuli and control timing of stimulation. A sound card converted the digital signal into an analog signal. A current source converted the analog voltage stimulus into a constant current stimulus. Either the experimenter or the subject could terminate electric stimulation by releasing a foot pedal connected to a safety switch. A transformer power supply (red circle and red lines) was used to isolate the subject from direct connection to the power line. An oscilloscope (green box and green line) was used to calibrate the equipment and monitor voltage delivered to the electrodes in real-time throughout the entire experiment. During calibration, before actual connection to the subject, a 1000-Ω resistor was connected to the output of the current source to ensure that the maximal output of the entire setup was exactly 2 mA and, under no circumstance, the current exceeded 2 mA. The 1000-Ω resistor was disconnected during the actual test session.

Electric stimulation was delivered to two electrodes, with one being the active electrode on either promontory or round window and the other being a reference electrode including one of the following 4 electrode types: (1) silver-chloride 2.3×3 cm plate (Natus Medical Inc., Pleasanton, Calif.), (2) gold cup (Natus Neurology-Grass, Warwick, R.I.), (3) gold-foil-wrapped-foam tiptrode (Etymotic ER3-26A, Elk Grove Village, Ill.), and (4) a platinum ball electrode to be placed in the middle ear cavity. In some embodiments, the reference electrode is placed remotely from the active electrode, but accessible during myringotomy.

The example in the right panel of FIG. 1 shows that electric stimulation was delivered to a gold-plated tiptrode inserted in the right ear canal and a plate electrode placed on the right mastoid. The stimulus was either a sinusoid or charge-balanced bi-phasic pulse train. The stimulus level varied from 0 to 2 mA or the maximal current that produced uncomfortable loudness or other sensations. The stimulus frequency varied from 10 to 10,000 Hz. The stimulus duration was 500 ms for initial psychophysical testing, namely finding threshold and uncomfortable loudness levels.

The psychophysical result was used to decide stimulus parameters for the tinnitus suppression experiment. The stimulus level was set at slightly softer than the tinnitus loudness if the stimulus produced a sufficiently loud auditory percept, or at the 2-mA maximal level that produced either much softer than the tinnitus loudness or no auditory percept at all. The stimulus frequency included a 100-Hz low frequency, a mid frequency (300, 500 or 700 Hz) and a 5000-Hz high frequency. The present stimulus duration was 2-3 minutes in most test sessions, or up to 10 minutes if there was sufficient time in the test session. The inter-session interval was 3 minutes or as long as needed until tinnitus returned to the baseline. In cases of extended residual inhibition longer than 30 minutes, the subject was released and instructed to report when tinnitus returned to the baseline. Stimulation was delivered to one of the following three sites, including (1) the tinnitus ear in unilateral cases, (2) the ear with more severe tinnitus in bilateral cases, or (3) both ears in bilateral cases by placing a tiptrode in each of the two ear canals (T1, T4 and T5).

Minimally-Invasive Electric Stimulation

Figure 2A:
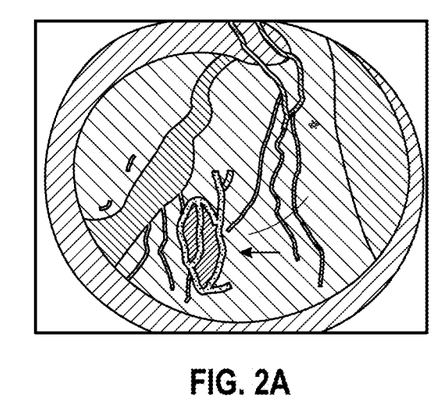
FIG. 2A shows a myringotomy (arrow) allowing an electrode to pass through the tympanic membrane; the umbo is labeled (asterisk).
Figure 2B:
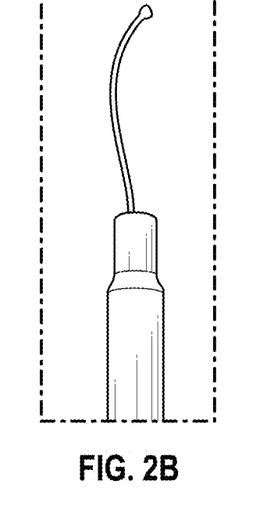
FIG. 2B shows a slightly bent ball electrode.
Figure 2C:
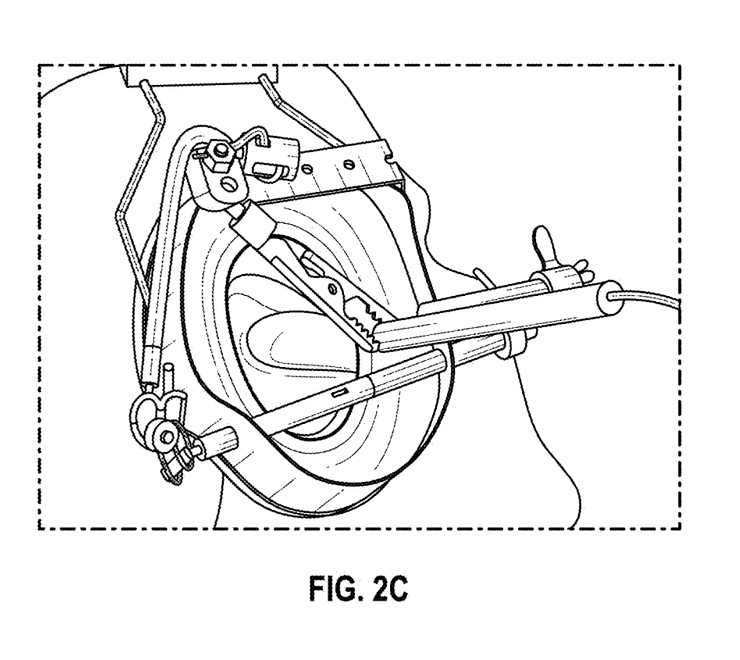
FIG. 2C shows a custom-made head-mounted electrode holder that holds the electrode and also shows the speculum and impression materials.

Except for placing a ball electrode on the promontory or round window, the minimally-invasive electric stimulation had an identical setup as the non-invasive stimulation. FIG. 2A shows a 1.5-mm myringotomy made in the tympanic membrane over the round window niche. The myringotomy was performed under local anesthesia by applying a thin film of phenol (Apdyne, Inc., Denver, Colo.) to the posterior-inferior quadrant of the tympanic membrane. FIG. 2B shows a platinum-iridium ball electrode, which had a diameter of 0.5 mm and was slightly bent to access the promontory or round window (Medtronic Yingling Flex Tip electrode REF8225251, Minneapolis, Minn.). The Medtronic electrode contained a flexible platinum-iridium wire that is fully insulated to the ball tip to prevent current shunting. FIG. 2C shows a customized head-mounted electrode holder that was modified from over-the-head/circumaural headphones and was used to keep the electrode steady and in close contact with the stimulation site during the experiment. The head-mounted electrode holder was placed on the subject and the position, tension and angle of the electrode holder was adjusted for comfort and access to the tympanic membrane, specifically the tympanostomy over the round window area. A 5-mm ear speculum (Welch Allyn Cat. No. 52135, Skaneateles Falls, N.Y.) was inserted into the ear canal, and stabilized with hearing aid impression material (Audiologist's Choice Cat. No. 01602, Chesterfield, Mo.) being applied to the concha and lateral cartilaginous ear canal around the speculum. The bent ball electrode was carefully placed through the tympanostomy and onto the promontory or round window membrane. In the round window case, the surgeon first identified the round window niche in the posterior-inferior quadrant of the tympanic membrane, then tectulum or the round window overhang, and finally placed the electrode on the round window membrane under the tectulum. Contact with the round window membrane was further confirmed by decreased and stable electrode impedance on the monitoring oscilloscope. At the end of the experiment, all materials were carefully removed by first pulling the electrode out of the middle ear, then disengaging the clamp holding the electrode to remove the electrode from the ear canal, and taking off the headphones. The impression material and speculum were removed afterwards. The tympanic membrane was patched using a standard technique of paper patch myringoplasty. Placement of a myringotomy in the office is a routine part of neurotology practice and is considered minimally invasive compared to other invasive operative procedures such as full middle ear exploration or cochlear implantation. None of the 5 subjects who underwent this minimally-invasive protocol reported any adverse events or complications during and after the experiment. The tympanic membranes healed in all 5 subjects who had myringotomy.

Procedures

Before each test session, the subject was reminded that he or she could terminate electric stimulation at any time during the experiment by releasing the food pedal connected to the safety switch. The subject first reported the baseline tinnitus loudness on a 0-10 scale, with 0 representing no tinnitus and 10 uncomfortable loudness. To study tinnitus suppression, the electric stimulus level was set at a loudness level that was 0-2 units below the tinnitus loudness, or the setup's maximal level of 2 mA if the stimulus could not produce such a loudness level. The subject reported loudness estimates of both tinnitus and the stimulus at the onset of electric stimulation and every 30 seconds after that until the end of stimulation. The subject continued to report tinnitus loudness at the offset of stimulation and every 30 seconds after that until tinnitus returned the baseline level. In situations where residual inhibition lasted longer than minutes or even hours, the subject was instructed to report via phone or email the time when his or her tinnitus returned to the baseline level.

Results

Non-Invasive Electric Stimulation (100-Hz)

The effect of 100-Hz sinusoidal electric stimulation on both stimulus and tinnitus loudness over a 2 to 5-minute duration in 4 subjects and 6 conditions was tested. Except for one condition in T4 where cup electrodes were placed between left and right temple, all other conditions used at least one tiptrode inserted in the ear canal. First, note loudness responses to electric stimulation. Except for T1 who experienced a slight increase in loudness from 3 to 4 during electric stimulation, all other subjects experienced loudness adaptation, or total adaptation without even noticing stimulus offset (T3 and T4). Second, note the effect of electric stimulation on tinnitus. Two subjects (T1 and T3) reported no effect of electric stimulation on tinnitus. Two subjects in 3 conditions (T2, T4, and T4) experienced slight reduction in tinnitus loudness (1-2 units) during electric stimulation. In one condition, T4 experienced the most ideal result using electric stimulation to treat tinnitus: both tinnitus and stimulus totally disappeared 1-3 minutes after the stimulation onset, with tinnitus being totally suppressed during the remaining period of stimulation and even after stimulation (e.g., residual inhibition).

Non-Invasive Electric Stimulation (300-700 Hz)

The effect of mid-frequency sinusoidal electric stimulation on both stimulus and tinnitus loudness over a time period of 2 to 5 minutes in 4 subjects was tested. The subjects experienced either stimulus loudness adaptation (T1, T4 and T5) or no adaptation (T3), with nobody reporting loudness enhancement. Except for a slight "rebound" (T1) and "inhibition" (T5) at the stimulation offset, the mid-frequency electric stimulation had no effect on tinnitus.

Non-Invasive Electric Stimulation (5000-Hz)

The effect of 5000-Hz sinusoidal electric stimulation on both stimulus and tinnitus loudness over a 2 or 3-minute duration in 4 subjects was tested. The subjects heard either a faint sound (T1) or nothing (T4-6) during the 5000-Hz electric stimulation. In terms of its effect on tinnitus, two subjects (T1 and T5) reported no change in tinnitus, one subject (T4) reported slight decrease in tinnitus loudness (from 3 to 2.5), while the remaining subject (T6) experienced a significant decrease in tinnitus loudness (from 4.5 to 0.5) with residual inhibition lasting for another 3 minutes.

Minimally-Invasive Electric Stimulation

Figure 3:
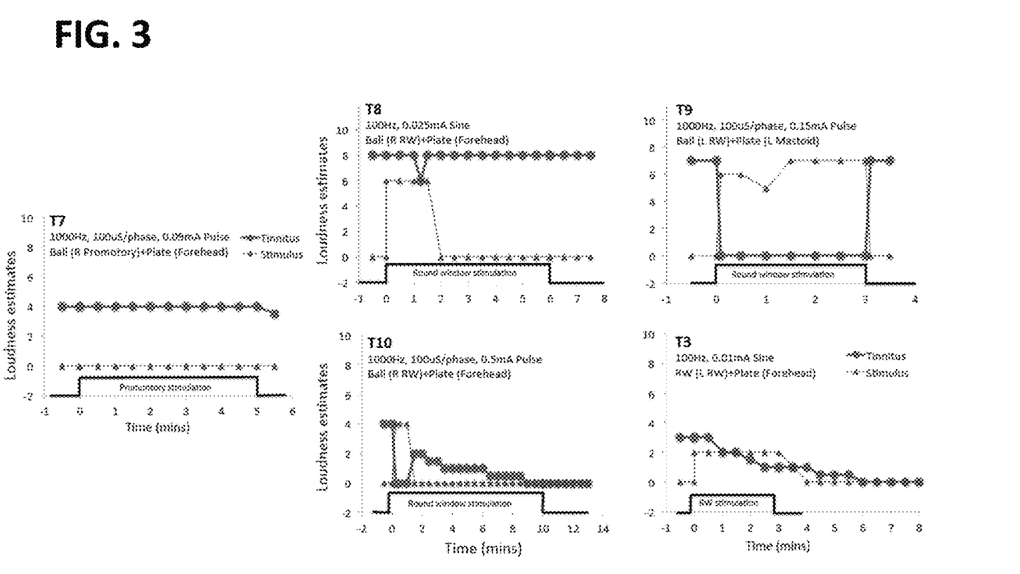
FIG. 3 shows the effect of promontory (T7) and round window (T8-10) electric stimulation on stimulus and tinnitus perception. Perceived loudness (y-axis) is plotted as a function of time (x-axis) for both tinnitus (red circles connected by the solid red line) and stimulus (blue triangles connected by the dotted blue line).

FIG. 3 shows the effect of minimally-invasive electric stimulation on both stimulus and tinnitus loudness in 4 subjects with unilateral hearing loss (T7-T10) and 1 subject with symmetrical sloping loss (T3). In T7, promontory electric stimulation did not produce any stimulus sensation or any change in tinnitus loudness, except for a slight decrease after the stimulus offset. However, T7 reported that electric stimulation made his tinnitus "less annoying and irritating." In the remaining 4 subjects (T8-10 and T3), round window stimulation was applied. T8 experienced total stimulus loudness adaptation 1.5 minutes after stimulus onset, and, at the same time, reported a slight decrease in tinnitus loudness, which quickly recovered to its usual value during the adaptation period of the stimulus and after electric stimulation. T9 did not show any stimulus loudness adaptation but reported total suppression of his tonal tinnitus component during the entire period of electric stimulation. However, this total suppression was likely a result of simultaneous auditory masking for three reasons. First, T9 matched the pitch of her tonal tinnitus to a pure tone of 1230 Hz, which was close to 1000 Hz of the electric stimulus frequency. Second, tinnitus loudness not only dropped to zero immediately at the stimulation onset but also recovered to its usual value immediately at the stimulation offset. Third, T9 reported that the 1000-Hz electric stimulation had no effect on the "musical" tinnitus component, which had a loudness rating of 4. T10 experienced the most ideal outcome. The electric stimulus totally adapted two minutes after the stimulation onset. The tinnitus loudness was zero during the first two minutes of stimulation, rebounded to half of its usual value at the moment of total stimulus adaptation, and gradually reduced to zero at the end of stimulation and afterwards. In addition, T10 reported 5 hours of residual inhibition in response to 10-minute round window electric stimulation. T3, the symmetrically impaired subject who did not experience any tinnitus suppression with non-invasive electric stimulation, reported significant tinnitus suppression in response to round window stimulation. Different from T10, T3 did not adapt to electric stimulation at all. Similar to T10, T3 reported gradual suppression of tinnitus during electric stimulation and total residual inhibition of tinnitus after electric stimulation. Surprisingly, much longer than T10's 5-hour residual inhibition, T3's total residual inhibition lasted 20 hours in response to 3-minute round window stimulation.

Discussion

For a total of 19 conditions in 10 tinnitus subjects (FIG. 6), 12 conditions or 63% produced some degree of tinnitus reduction, 6 or 32% had no effect on tinnitus, and 1 or 5% increased tinnitus.

Figure 4:
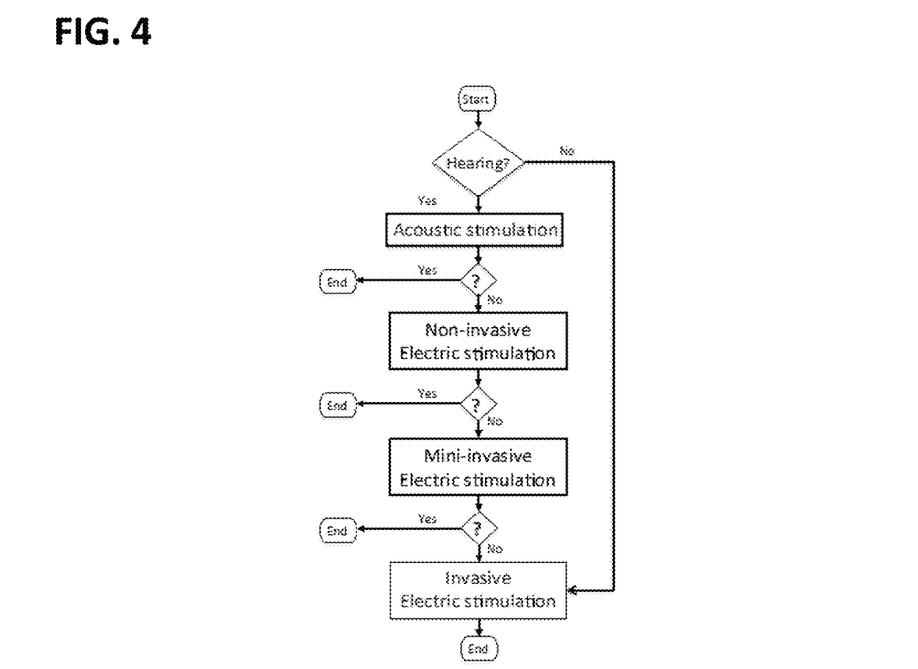
FIG. 4 shows a schematic of an example of a method for treating tinnitus. The method analyzes a tinnitus sufferer's hearing status and uses progressively more invasive stimulation dependent upon his or her response to the stimulation. The present invention is not limited to the method in FIG. 5.

Given various degrees of hearing loss in tinnitus sufferers and the equally various degrees of effectiveness in tinnitus therapy, it is important to develop a systematic approach to tinnitus treatment. To illustrate this point, T5, who was not responsive to either mid- or high-frequency electric stimulation, actually responded effectively to pitch-matched sound stimulation. T3 was another example of the need for a systematic treatment strategy, where the non-invasive electric stimulation was totally ineffective (FIG. 3) but the minimally-invasive stimulation produced not only immediate tinnitus suppression but also prolonged residual inhibition (FIG. 3). FIG. 4 shows a potential treatment strategy that takes both hearing loss and tinnitus therapy effectiveness into account.

For example, a patient suffering from tinnitus will have a hearing evaluation. If there is no functional hearing, then the person will go straight to the "invasive electric stimulation" intervention such as a cochlear implant to treat both deafness and tinnitus. If there is significant hearing, then the person will first try sound therapy or "acoustic stimulation" to evaluate its effectiveness. The person ends with sound therapy if it is effective, but if it is not, then he or she will try "non-invasive Electric stimulation" by placing electrodes on the scalp or in the ear canal or the eardrum. Similarly, the person ends with the non-invasive electric stimulation if it is effective, but if it is not, he or she will try "minimally-invasive electric stimulation" by making a small myringotomy and placing an electrode on the promontory or round window. The person ends with the minimally-invasive electric stimulation if it is effective, but if it is still not, then he or she may consider invasive electric stimulation from cochlear implantation to vagus nerve or deep brain stimulation for the purpose of treating tinnitus. If a tinnitus sufferer indeed ends here, he or she needs to consider the balance between the benefit of tinnitus relief and the risk of surgery or losing hearing. At present, cochlear implantation is not applicable to tinnitus sufferers with normal hearing.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. An electrical stimulation system (100) comprising:
   a. an electrode (110) or electrodes shaped to hook underneath one or more bones of an outer surface of an inner ear to directly contact at least a portion of the inner ear;
   b. a microprocessor disposed in a receiver (120) operatively connected to the electrode (110) and disposed adjacent or near-adjacent to the electrode (110), wherein the receiver (120) is implanted at the outer surface of the inner ear, wherein the microprocessor sends a first signal to the electrode (110) to cause the electrode (110) to deliver stimulation to a portion of an ear;
      wherein the electrode (110) and the receiver (120) comprise an implantable portion of the system (100) disposed at the outer surface of the inner ear;
      wherein the implantable portion is immobilized by one or more anchors (125), the one or more anchors (125) having a V shape, wherein the implantable portion is disposed at a vertex of the V shape; and
   c. a transmitter (130) comprising a power source operatively connected to the receiver (120) and the electrode (110) disposed in an ear canal (230), wherein the power source delivers energy to the receiver (120);
      wherein the stimulation delivered by the electrode (110) helps reduce or eliminate tinnitus.

2. The system of claim 1, wherein the electrode (110) is a platinum-iridium or other biocompatible conductive material ball electrode.

3. The system of claim 1, wherein the signal is transmitted optically, magnetically, via radiofrequency.

4. The system of claim 1, wherein the receiver (120) is 0.1 to 100 cm from the electrode (110).

5. The system of claim 1, wherein the electrode (110) delivers electrical, visible or invisible light, magnetic, or radiofrequency stimulation.

6. The system of claim 1, wherein the electrode (110) delivers stimulation to the inner ear (220).

7. The system of claim 1, wherein a user can turn the electrode(s) on or off as needed using an external or internal control device, software, or system.

8. The system of claim 1, wherein a control device is wired or wirelessly operatively connected to the transmitter (130), the control device functions to turn on and off the transmitter and/or the electrode (110).

9. The system of claim 8, wherein the control device signals the transmitter to present each frequency, shape, duration, pulse, and/or amplitude signals for a period of time and asks for a response from the user on a degree of tinnitus and side effects of stimulation on a user interface.

10. The system of claim 9, wherein the control device, system, or software can toggle, control, or change a frequency, shape, duration, pulse, and/or amplitude of the current delivered by the system (100).

11. The system of claim 1, wherein the electrode (110) is additionally able to directly contact the surface of the outer wall of the cochlea, or oval window.

12. The system of claim 1, wherein the electrode (110) may have its own power source implanted which could be charged from an external device.

13. The system of claim 1, wherein one or more parameters of the signal can be changed by another individual in a wired or wireless manner.

14. The system of claim 1, wherein the implantable portion of the device can be delivered through the tympanic membrane.

15. The system of claim 1 which adjusts one or more parameters of the signal based on measurements made by the implanted electrode (110).

16. The system of claim 1 further comprising a fixation mechanism configured to be placed at the outer surface of the inner ear to affix a component at the outer surface of the inner ear;
   wherein the electrode (110) is configured to be immobilized at the outer surface of the inner ear to treat tinnitus via the fixation mechanism (125).

17. A method of treating tinnitus in a patient in need thereof, said method comprising:
   a. implanting a stimulation system (100) comprising:
      i. an electrode (110) or electrodes shaped to hook underneath one or more bones of an outer surface of an inner ear to directly contact at least a portion of the inner ear,
      ii. a microprocessor disposed in a receiver (120) operatively connected to the electrode (110) and disposed adjacent or near-adjacent to the electrode (110), wherein the receiver (120) is implanted at the outer surface of the inner ear, wherein the microprocessor sends a first signal to the electrode (110) to cause the electrode (110) to deliver stimulation to a portion of an ear, iii. a transmitter (130) comprising a power source operatively connected to the receiver (120) and the electrode (110) wherein the transmitter (130) is disposed in an ear canal (230), wherein the power source delivers energy to the receiver (120), and
iv. a control device wirelessly-operatively connected to the transmitter (130),
wherein the electrode (110) is in direct contact with a round window (210) without completely obstructing the round window (210);
b. immobilizing the receiver (120) in the ear of the patient by a plurality of anchors (125) such that the electrode (110) does not move around;
c. using the control device to determine a stimulation setting to provide maximum tinnitus relief to the patient; and
d. sending a signal with the stimulation setting to the transmitter (130) and receiver (120) to be executed by the electrode (110) to provide stimulation to the round window (210).

18. The method of claim 17, wherein the stimulation system (100) sends a minimum amount of stimulation to the ear to remedy tinnitus.

19. The method of claim 17, wherein the control device can toggle, control, or change a frequency, shape, duration, pulse, and/or amplitude of the current delivered by the system (100).

* * * * *